US010663459B2

(12) United States Patent
Park et al.

(10) Patent No.: US 10,663,459 B2
(45) Date of Patent: May 26, 2020

(54) COMPOSITION FOR DETECTING MICROBIAL CONTAMINATION COMPRISING PREPARATION FOR DETECTING NUCLEASES, AND USE THEREOF

(71) Applicant: Haesung Bio Co., Ltd., Daejeon (KR)

(72) Inventors: Kyoung Sook Park, Daejeon (KR); Bong Hyun Chung, Seoul (KR); Kyung Jin Lee, Chungcheongnam-do (KR); Byung Kwon Kim, Daejeon (KR); So Yeon Yi, Daejeon (KR); Jung Sun Kwon, Daejeon (KR); Ui Jin Lee, Daejeon (KR); Seong U. Kim, Seoul (KR); Ho Jae Lee, Seoul (KR)

(73) Assignee: Haesung Bio Co., Ltd., Daejeon (KR)

( * ) Notice: Subject to any disclaimer, the term of this patent is extended or adjusted under 35 U.S.C. 154(b) by 115 days.

(21) Appl. No.: 15/563,717

(22) PCT Filed: Apr. 7, 2016

(86) PCT No.: PCT/KR2016/003661
§ 371 (c)(1),
(2) Date: Dec. 7, 2017

(87) PCT Pub. No.: WO2016/163781
PCT Pub. Date: Oct. 13, 2016

(65) Prior Publication Data
US 2019/0033302 A1   Jan. 31, 2019

(30) Foreign Application Priority Data
Apr. 8, 2015 (KR) .................. 10-2015-0049614

(51) Int. Cl.
| | | |
|---|---|---|
| *C12Q 1/68* | (2018.01) | |
| *G01N 33/53* | (2006.01) | |
| *C12Q 1/689* | (2018.01) | |
| *C12Q 1/04* | (2006.01) | |
| *C12Q 1/22* | (2006.01) | |

(52) U.S. Cl.
CPC ........... *G01N 33/5308* (2013.01); *C12Q 1/04* (2013.01); *C12Q 1/22* (2013.01); *C12Q 1/689* (2013.01); *G01N 2333/922* (2013.01); *Y02A 50/451* (2018.01)

(58) Field of Classification Search
None
See application file for complete search history.

(56) References Cited

U.S. PATENT DOCUMENTS

2011/0319290 A1* 12/2011 Raymond ............ C12Q 1/6869
506/9

FOREIGN PATENT DOCUMENTS

| CN | 102154489 A | 8/2011 |
|---|---|---|
| KR | 10-2011-0048734 A | 5/2011 |
| KR | 10-2012-0018018 | 2/2012 |
| WO | WO 2013/033436 A1 | 3/2013 |
| WO | 2015120406 A1 | 8/2015 |

OTHER PUBLICATIONS

International Search Report for International Application No. PCT/KR2016/003661, "Composition for Detecting Microbial Contamination Comprising Preparation for Detecting Nucleases, and Use Thereof", 2 pgs, dated Aug. 12, 2016.
Sato, et al., "Highly sensitive Nuclease Assays based on Chemically modified DNA or RNA", *Sensors*, 14: 12437-12450 (Jul. 11, 2014).
Ray, et al., "Gold Nanoparticle based FRET Assays for the Detection of DNA Cleavage", *The Journal of Physical Chemistry B*, 110: 20745-20748 (2006).
International Preliminary Report on Patentability for International Application No. PCT/KR2016/003661, "Composition for Detecting Microbial Contamination Comprising Preparation for Detecting Nucleases, and Use Thereof", 17 pgs, dated Oct. 10, 2017.
Written Opinion for International Application No. PCT/KR2016/003661, "Composition for Detecting Microbial Contamination Comprising Preparation for Detecting Nucleases, and Use Thereof", dated Aug. 12, 2016.

* cited by examiner

*Primary Examiner* — James Martinell
(74) *Attorney, Agent, or Firm* — Hamilton, Brook, Smith & Reynolds, P.C.

(57) ABSTRACT

The present invention relates to a composition for detecting microbial contamination comprising a preparation for detecting nucleases, and a use thereof. A probe for measuring nucleic acid double-stranded nucleases, according to the present invention, may detect the comprehensive nucleic acid degradation capability of nucleases, whereby it is possible to quickly and precisely detect and quantify live microorganisms in a sample in a simple manner. Moreover, since the probe of the present invention is characterized in that signals of fluorescence consistently increase; is capable of measuring live microorganisms; and consists of a double-stranded nucleic acid, the probe is excellent for storage in a kit or a cartridge. As such, it is expected that the probe of the present invention may be used to easily and simply measure and compare the degree of contamination of microorganisms in an environment.

9 Claims, 6 Drawing Sheets
Specification includes a Sequence Listing.

COMPOSITION FOR DETECTING MICROBIAL CONTAMINATION COMPRISING PREPARATION FOR DETECTING NUCLEASES, AND USE THEREOF

This application is the U.S. National Stage of International Application No. PCT/KR2016/003661, filed Apr. 7, 2016, which designates the U.S., published in Korean, and claims priority under 35 U.S.C. §§ 119 or 365(c) to Korean Application No. 10-2015-0049614, filed Apr. 8, 2015. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:

a) File name: 55021000001 CORRECTEDSEQUENCELISTING.txt; created Jan. 19, 2018, 1.67 KB in size.

TECHNICAL FIELD

The present invention relates to a composition for detecting microbial contamination comprising an agent for detecting nuclease in microorganism and uses thereof.

BACKGROUND ART

The general public is highly interested in health and hygiene as the level of income increases. However, it is not easy for them to personally detect and quantitatively evaluate microorganisms that are invisible to the naked eye.

Various microorganisms inhabit daily items such as hair combs, cell phones, desks, clothes with which a human being uses, or spaces such as bathrooms, bedrooms, or those microorganisms are present even in the air. Such microorganisms are likely to contain opportunistic pathogen and pathogenic bacteria, and the like.

Traditional methods for measuring the amount of microorganisms include a standard plating method in which a sample taken from an environment is serially diluted and smeared on a medium capable of culturing microorganisms, and 2 or 3 days later, the number of colonies produced from the medium is calculated to estimate the amount of microorganisms. Such traditional methods have disadvantages that they require specialized experimental tools and skilled technicians as well as a very long time, thereby making it difficult for the general public to quickly measure living microorganisms.

Recently, several methods have been developed to solve the problems associated with conventional methods. Such methods indirectly measure the amount of microorganisms by measuring the amount of various constituent substances which are constitutively present in cells.

One representative method is to perform a measurement based on the amount of ATP. ATP is a useful substance for measuring the amount of cells in a sample, since it is used as a major source of bioenergy in cells and is a constituent which all organisms have in common. Due to these advantages, an ATP-based measurement method is widely used for quantitative measurement of microorganisms. In order to measure ATP, a luciferase enzyme is generally used to induce luminescence reaction and quantification is made through intensity of light. In this case, luciferin is used as a substrate.

However, the ATP-based method has disadvantages that ATP in a reaction sample is rapidly depleted and thus signals do not last for a long time, and production costs of the enzyme and substrate to be added are high. In addition, there is a problem that it has limited storability due to the reason that the constituent used for measurement is an enzyme. There is another problem in the method of quantifying microbial cells through such ATP measurement. That is, microorganisms that are dead or have a very low viability are most likely to be measured as well, since the function of ATP is maintained even if cells are dead.

Another method is to use ligases. This method is initiated by adding specific DNA fragments into a sample. Then, ligases in cells recognize the DNA fragments and ligate two fragments through polymerization reaction. It is known that when real-time PCR analysis is performed for the thus ligated fragments using specific primers, it is possible to evaluate the amount of microorganisms at even $10^3$ cells.

However, as in the case of the measurement methods performed through luciferase, this method has difficulty with respect to storage since it uses ligase which is an enzyme. Also, in order to identify new nucleic acid molecules produced by the reaction of ligases with DNA strands, RT-PCR and PCR, gel electrophoresis procedure are needed, thereby requiring expensive equipment and skilled technicians as well as a very long time for analysis. Further, since ATP molecules are also present on dead cells as in the measurement method using luciferase, it has a disadvantage that it is not possible to measure only living microorganisms.

Accordingly, in order to solve such problems, it is desirable to estimate the detection and/or quantity of microorganisms by measuring the amount and activity of an enzyme that is constitutively present in cells.

(Prior art Document) Patent Application No. KR1020100081068

DISCLOSURE

Technical Problem

For this purpose, the present inventors have made intensive efforts to develop a method for detecting living microorganisms and measuring the amount thereof in a very quick and effective way without expensive equipment and skilled technicians. As a result, the present inventors developed a double-stranded nucleic acid probe and have found that the probe is capable of detecting the nucleic acid degradation ability of nucleases in living microorganisms in a precise and effective way, thereby completing the present invention.

Technical Solution

Accordingly, an object of the present invention is to provide a composition for detecting microbial contamination, in which the composition includes an agent for detecting nuclease in microorganism.

Another object of the present invention is to provide a kit for detecting microbial contamination.

A further object of the present invention is to provide a method for detecting microbial contamination.

A still further object of the present invention is to provide an oligonucleotide for measuring nuclease activity.

Advantageous Effects

The composition for detecting microbial contamination, in which the composition includes an agent for detecting nuclease in living microorganisms has features that it is capable of detecting comprehensive nucleic acid degradation ability of nucleases, thereby making it possible to detect and quantify living microorganisms in a sample in a very quick and precise way, and that it makes the detection method simple. Furthermore, the probe of the present invention exhibits a feature that fluorescence signals consistently increase, is capable of measuring living bacteria, and allows a kit or cartridge to have an excellent storability due to the reason that it consists of a double-stranded nucleic acid. Accordingly, it is expected that the composition of the present invention may be used to measure and compare the degree of microbial contamination in an environment in an easy and simple way.

MODES OF THE INVENTION

The present invention will be described in detail below.

According to an aspect of the present invention, the present invention provides a composition for detecting microbial contamination, in which the composition includes an agent for detecting nuclease in microorganism.

According to a preferred embodiment of the present invention, the composition of the present invention may be used for detecting living microorganisms.

In other words, a feature of the present invention is to detect and/or quantify microorganisms using nuclease which is an enzyme present in a living microorganism.

Normally, methods for quantifying microorganisms used in the art lead to false positive results, because the function of ATP is maintained even if cells are dead, and thus microorganisms that are dead or have a very low viability are also measured.

However, since the composition of the present invention is capable of detecting and quantifying only substantially living microorganisms in a quick and easy way, it is possible to solve the problem of leading to false positives as described above.

In the present invention, the microorganisms mean bacteria or fungi.

The type of bacteria that can be detected by the composition of the present invention is not limited. Specifically, the bacteria may be a Gram-negative bacteria or a Gram-positive bacteria.

Examples of the Gram-negative bacteria may include *Escherichia coli* (*E. coli*), *Helicobcater, Hemophilus, Neisseria, Cyano bacteria, Klebsiella, Acetobacter, Enterobacter, Chlamydia, Vibrio, Pseudomona, Salmonella, Thiobacter, Borrelia, Burkholderia, Serratia, Treponema*, and the like. Examples of the Gram-positive bacteria include *Bacillus, Nocardia, Clostridium, Propionibacterium, Actinomyces, Enterococcus, Cornyebacterium, Listria, Lactobacillus, Gardnerella, Mycobacterium, Mycoplasma, Staphylococcus, Streptomyces, Streptococcus*, and the like.

The fungi that can be detected by the composition of the present invention is not limited. For example, the fungi may include phytopathogenic fungi such as *Fusarium* spp., *Penicillium* spp. or *Rhizoctonia solani*, and animal pathogenic fungi such as *Candida* spp., *Aspergillus* spp., *Cryptococcus neoformans*, and *Trichophyton* spp., and the like.

According to a preferred embodiment of the present invention, the agent for detecting nuclease consists of an oligonucleotide.

According to a preferred embodiment of the present invention, the oligonucleotide consists of a single strand or a double strand.

As used herein, the term "oligonucleotide" used with reference to an agent for detecting nuclease means a probe.

In the present invention, the probe is, preferably, characterized in that one strand of the double-stranded oligonucleotide comprises a blunt end at the 5'-end or 3'-end; and the other strand of the double-stranded oligonucleotide comprises a sticky end on the opposite end of the blunt end; and a nucleic acid mismatch is present between the blunt end and the sticky end.

As used herein, the term "5'-end" site used with reference to a probe means a site or region that includes a contiguous sequence of any length from the 5'-end of the probe. Preferably, the 5'-end site of a probe consists of a sequence including 1 to 10 nucleotides from its 5'-end.

As used herein, the term "3'-end" site used with reference to a probe means a site or region that includes a contiguous sequence of any length from the 3'-end of the probe. Preferably, the 3'-end site of a probe consists of a sequence including 1 to 10 nucleotides from its 3'-end.

In the present invention, a nucleic acid strand refers to an oligonucleotide, a nucleotide or a polynucleotide, and fragments or portions thereof. Also, it refers to DNA or RNA of genomic or synthetic origin which may mean a sense or antisense strand. In the present invention, the nucleic acid strand may preferably consist of DNA.

Further, the probe of the present invention is preferably characterized that it consists of a nucleic acid double strand. The nucleic acid double strand of the present invention is mutually hybridized. As used herein, the term "hybridization" is used in connection with paring of complementary nucleic acids. The hybridization and hybridization strength (i.e., the association strength between nucleic acids) are affected by factors such as the degree of complementarity between the nucleic acids, the stringency of the relevant conditions, and the Tm of the hybrid formed. The "hybridization" method involves an annealing of one nucleic acid to another complementary nucleic acid, that is, a nucleic acid having a complementary nucleotide sequence. The ability of two nucleic acid polymers including complementary sequences to recognize each other and to anneal through base-paring interaction is a well understood phenomenon. Initial observations of the "hybridization" process (Marmur and Lane, Proc. Natl. Acad. Sci. USA 46:453 (1960) and Doty et al., Proc. Natl. Acad. Sci., USA, 46: 461 (1960)) have been progressed by subsequent researches and have become an essential tool for modern biology.

The nucleic acid strand of the present invention may contain therein the bases that are not generally found in natural nucleic acids, for example, inosine and 7-deazaguanine. A perfect complementarity is not necessary; stable duplexes may contain a mismatched base pair or a non-paired base. Those skilled in the art of nucleic acid technology can determine duplex stability empirically considering a number of variables including, for example, the length of an oligonucleotide, the base composition and sequence of an oligonucleotide, ionic strength, and incidence of mismatched base pairs.

The length of the nucleic acid strand of the present invention is not limited, and it is preferable to have the length to the extent that a quencher and a fluorescent material, which may be present at both ends of the probe, do not affect each other. Thus, preferably, it may consist of 31-mer or more nucleic acids. For example, it may consist of 31 to 60, 31 to 50, or 31 to 40 nucleic acids.

The nucleic acid strand of the present invention may be produced in any manner, for example by chemical synthesis, DNA replication, reverse transcription, PCR, or a combination thereof.

In the present invention, nuclease refers to a nucleic acid hydrolase, which means an enzyme that catalyzes the hydrolytic reaction of nucleic acids, nucleotides, nucleosides, and the like. The nuclease has no limitation in its type, and includes a DNase that degrades DNA and a RNase that degrades RNA. In addition, the nuclease is a concept including polynucleotidases, nucleotidases, and nucleosidases. It also includes an exonuclease that sequentially degrades from the 3'- or 5'-end and an endonuclease that cleaves the inside of the nucleic acid chain. In particular, the present invention encompasses configurations capable of simultaneously measuring exonucleases or endonucleases.

In the present invention, a blunt end means the end of a nucleic acid double strand where no single strand is present. In the oligonucleotide, that is, probe, of the present invention, the blunt end may be present at the 3'-end or the 5'-end.

In the present invention, a sticky end means the end of a nucleic acid double strand where a single-stranded chain (3' or 5' overhang) is present at its end, in which the length of the overhang single chain is not limited. In addition, the sticky end is located at an opposite end to the end where the blunt end is present, that is, when the blunt end is present at the 3'-end, the sticky end may be present at the 5'-end, and when the blunt end is present at the 5'-end, the sticky end may be present at the 3'-end. Further, the sticky end may contain a nucleic acid mismatch at the non-overhanging end, which is constructed to cause 3'→5' nucleic acid degradation action that forms a part of the correction operation by a DNA polymerase. The nucleic acid mismatch may be one or more, and the mismatch may be preferably given to maintain a distance between the fluorescent material and the quencher such that their actions are not inhibited.

As used herein, the term "nucleic acid mismatch" or "mismatched nucleotide" means a non-complementary nucleotide or a nucleotide that is recognized as a mismatch by a template-dependent nucleic acid polymerase with proofreading activity.

The mismatched nucleotide may be at various sites of the probe.

In an embodiment of the present invention, in order to identify endonuclease activity, a nucleic acid mismatch is given between the blunt end and the sticky end on the double-stranded nucleic acid probe. The nucleic acid mismatch means that complementary binding of nucleic acids has not occurred. In the present invention, the mismatch is not limited in terms of the number and length of the nucleic acid, and is preferably 1 or more, more preferably 1 to 10, most preferably 3.

According to a preferred embodiment of the invention, the mismatched nucleotide is located at a position spaced 1 to 10 nucleotides away from its 3'-end.

If there are at least two mismatched nucleotides in the oligonucleotide, the mismatched nucleotides may be located contiguously or non-contiguously.

In addition, the oligonucleotide of the present invention may have a fluorescent material and a quencher, attached to its 3'-end, 5'-end, both ends, or anywhere between both ends.

In the present invention, the fluorescent material is a substance that generates fluorescence when it is physically distanced from the quencher, and the type thereof is not limited. Examples of the fluorescent material include a luminous molecule, a metal ion, a complex compound, an organic dye, a conductor, a semiconductor, an insulator, a quantum dot, a quantum wire, and the like which emit light at their excited state.

Examples of the fluorescent material include fluorescent proteins such as enhanced green fluorescent protein (EGFP), enhanced cyan fluorescent protein (ECFP), enhanced blue fluorescent protein (EBFP), enhanced yellow fluorescent protein (EYFP), and red fluorescent protein (RFP).

Also, examples of the fluorescent material may include Pyrene or its derivatives, Cyanine (Cy) series, Alexa Fluor series, BODIPY series, DY series, rhodamine or its derivatives, Fluorescein or its derivatives, coumarin or its derivatives, Acridine homodimer or its derivatives, Acridine orange or its derivatives, 7-aminoactinomycin D (7-AAD) or its derivatives, Actinomycin D or its derivatives, 9-amino-6-chloro-2-methoxyacridine (ACMA) or its derivatives, DAPI or its derivatives, Dihydroethidium or its derivatives, Ethidium bromide or its derivatives, Ethidium homodimer-1 (EthD-1) or its derivatives, Ethidium homodimer-2 (EthD-2) or its derivatives, Ethidium monoazide or its derivatives, Hexidium iodide or its derivatives, bisbenzimide (Hoechst 33258) or its derivatives, Hoechst 33342 or its derivatives, Hoechst 34580 or its derivatives, hydroxystilbamidine or its derivatives, LDS 751 or its derivatives, Propidium iodide (PI) or its derivatives, Calcein or its derivatives, Oregon Green or its derivatives, Magnesium Green or its derivatives, Calcium Green or its derivatives, JOE or its derivatives, tetramethylrhodamine or its derivatives, TRITC or its derivatives, TAMRA or its derivatives, Pyronin Y or its derivatives, Lissamine or its derivatives, ROX or its derivatives, Calcium Crimson or its derivatives, Texas Red or its derivatives, Nile Red or its derivatives, Thiadicarbocyanine or its derivatives, dansylamide or its derivatives, cascade blue, 4', 6-diamidino-2-phenylindole (DAPI).

A quantum dot may be used as the fluorescent material. The quantum dot is a particle, which is formed largely of nano-sized II-IV or III-V semiconductor particles, and consists of a core of about 2 to 10 nm in size and a shell mainly composed of ZnS, etc. Even if the same material is used, fluorescence wavelength may vary depending on the particle size, and thus a various range of wavelength may be obtained. The Group II-VI or Group III-V compounds forming the quantum dot may be selected from the group consisting of CdSe, CdSe/ZnS, CdTe/CdS, CdTe/CdTe, ZnSe/ZnS, ZnTe/ZnSe, PbSe, PbS InAs, InP, InGaP, InGaP/ZnS and HgTe, and may be in the form of a single core or a core/shell.

In the present invention, the term "quencher" may be used as a light extinguisher, a light absorber or the like, meaning a substance that absorbs energy or light from a fluorescent material or a light source. The quencher may be a light absorbing protein, a light absorbing molecule, a metal nano-particle, a carbon particle, or the like. Preferably, the quencher may be any one selected from the group consisting of BLACK HOLE QUENCHER® (Biosearch Technologies, Inc.) (BHQ)-1, DABCYL, ECLIPSE® (ELITechGroup), TAMRA® (Life Technologies, Inc.), QSY-7, BLACK HOLE QUENCHER® (BHQ)-2, BLACK HOLE QUENCHER® (BHQ)-3, and Gold nano-particle, and the type thereof is not limited as long as it can absorb energy or light emitted from the labeling substance. In an embodiment of the present invention, BHQ-1 was used. The quencher is coupled to N-acetylmuramic acid (NAA) and may be linked to a peptidoglycan through N-acetylmuramic acid (NAA), but not limited thereto.

Further, according to another aspect of the present invention, the present invention provides a kit for detecting microbial contamination including the composition.

The kit of the present invention may be used for detecting microorganisms.

The kit of the present invention provides a kit for the storage or delivery of reaction components necessary to perform microbial detection. The kit may include any and all components necessary or desirable for detection, including, but not limited to, reagents themselves, buffers, control reagents (for example, tissue samples, positive and negative control target oligonucleotides, etc.), solid supports, labels, written and/or drawn instructions for use and product information, inhibitors, labeling and/or detecting reagents, packaging environment controls (for example, ice, dehumidifiers, etc.), and the like.

Since the kit of the present invention includes the above-described composition as a constituent, redundant contents are omitted in order to avoid excessive complexity of the present disclosure.

Further, according to another aspect of the present invention, the present invention provides a method for detecting microbial contamination, in which the method includes the steps of:

(a) treating a sample with the composition; and
(b) identifying fluorescence development in the sample.

In the present invention, the term "sample" is used in its broadest sense. On the one hand, it is meant to include specimens or cultures (for example, microbial cultures). On the other hand, it is meant to include both biological and environmental samples. The sample may include a specimen of synthetic origin.

Biological samples may be sterilized liquid and solid food and feed products, and components such as dairy items, vegetables, meat and meat products, and waste. Biological samples may be obtained from all livestock of various families, including feral or wild animals, including, but not limited to, marsupials, mammals such as lagomorphs, bear, fish, rodents, and the like.

Environmental samples include environmental materials such as surface matter, soil, water, and industrial samples, along with food and dairy product processing apparatuses, utensils, equipment, instruments, disposable and non-disposable items. These examples should not be construed as limiting the types of samples to which the present invention can be applied.

The method of the present invention may include the step of identifying the fluorescence development in the sample. As for the fluorescence development, the luminescence of the fluorescent material is restricted by the quencher of the probe, and the action of the quencher disappears at the time when the probe is cleaved by a nuclease, thereby allowing the fluorescence development to be identified.

In the method of the present invention, detection is made using the above-described composition. Thus, redundant contents are omitted in order to avoid the excessive complexity of the present disclosure.

Moreover, according to still further aspect of the present invention, the present invention provides a probe consisting of a double-stranded nucleic acid oligonucleotide for measuring nuclease activity, as described above.

The probe is an oligonucleotide for measuring nuclease activity, the oligonucleotide having a nucleic acid double strand, in which a blunt end is present at the 5'- or 3'-end; a sticky end is present at an opposite end to the end where the blunt end is present; and one or more nucleic acid mismatches are present between the blunt end and the sticky end.

The double-stranded nucleic acid probe for measuring nuclease activity according to the present invention has features that it is capable of detecting comprehensive nucleic acid degradation ability of nucleases, thereby making it possible to detect and quantify microorganisms in a sample in a very quick and precise way, and that it makes the detection method simple. Accordingly, it is expected that the probe may be used to measure and compare the degree of microbial contamination in an environment in an easy and simple way.

The present invention will be described in more detail below with reference to examples. However, these examples are given to illustrate the present invention, and the scope of the present invention is not limited to these examples.

EXAMPLE 1

Design and Synthesis of Probes

Pairs of fluorophore and quencher were placed at both ends of a double-stranded probe to measure the comprehensive nucleic acid degradation ability. The quenchers present at both ends of the probe were used at a length of 31 to 40-mers in total nucleotide sequence to constitute the probe so as not to affect the fluorophores present at the ends in an opposite direction (that is, so as to maintain a distance of more than 100 Å). One of both ends of the double strand was constructed to have a blunt-end structure so that a double strand DNA exonuclease could act thereon and the other was constructed to have a sticky-end structure so that the 5'-end is exposed to be degradable by a single strand DNA exonuclease.

In addition, a mismatch was allowed to occur at the 3'-end of the sticky end in order to cause 3'→5' nucleic acid degradation action that forms a part of the correction operation by a DNA polymerase. However, only one mismatch was given, since when the complementary nucleotide sequence is spaced 3 or more bases away from the 5'-end, an effect of the quencher is reduced. In order to cause endonucleases to exert their degradation effects in addition to exonucleases, the probe was constructed to have three mismatched nucleotides (mismatched bases) therein.

Figure 1:
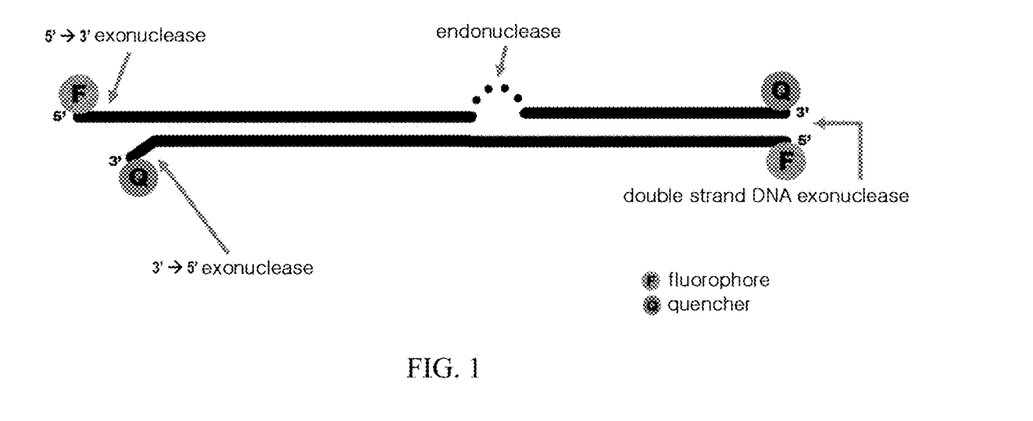
FIG. 1 is a schematic view of a double-stranded nucleic acid probe for nuclease measurement according to the present invention.

The construction of a double-stranded nucleic acid probe according to the present invention is illustrated in FIG. 1.

The sequences of the probes constructed in this example are as follows:

Double-stranded probe sense sequence (SEQ ID NO: 1) 5'-ACA TTA AGT GTA CCAGCT GCA TGA AAG TAC TTA ATA -3'; and Double-stranded probe antisense sequence (SEQ ID NO: 2) 5'-TAT TAA GTA CTT TCA TGC AAACGG TAC ACT TAA TA -3'.

(The underlined indicates mismatched nucleotides.)

The constructed probes of the present invention are characterized in that "a nucleic acid mismatch exists between the blunt end and the sticky end". When a mismatched sequence is inserted into one strand in an actual nucleic acid double strand, the strand does not match its complementary strand, thereby causing a mismatch to occur at both strands. That is, in the present invention, a mismatch means that two complementary strands are not bound to each other but are separated.

In addition, in the case of the double-stranded nucleic acid probe, the indicated length of the sense was 36-mer (or 44-mer which was used in Experimental Examples below), and the length of the antisense was designed to be shorter so that a nuclease acts well on the sticky end portion. Thus, the sense and the antisense have different lengths.

Further, each single-stranded DNA having a fluorophore-labeled and a quencher-labeled at its ends was synthesized and annealed to prepare a double-stranded DNA under the following condition:

1. 20 pmol of each oligomer being added to annealing buffer (10 mM Tris (pH 8.0), 50 mM NaCl, 1 mM EDTA, 2.5 mM $MgCl_2$);
2. Denatured at 95° C. for 5 minutes;
3. Cooled slowly to 25° C. over 2 to 4 hours.

EXAMPLE 2

Preparation of Samples

Microbial cells were recovered through centrifugation from the microbial culture (*E. coli* culture: absorbance of 1.3 to 1.7) cultured in LB at 37° C. by shaking-culture.

Crude extracts were recovered from the microbial culture through a chemical method using lysozyme (10 mg/ml) and a common commercial cell lysis buffer, and sonication.

The chemical method was performed as follows. After centrifugation, the supernatant was removed and only the cell pellet was recovered. 100 µl of a mixture of 998 µl of bacterial lysis buffer and 2 µl of lysozyme (10 mg/ml) was added to the cell pellet and cell lysis was performed for 10 minutes. Then, centrifugation was performed at 12,000 rpm for 15 minutes to separate only water-soluble proteins. Also, the sonication was performed as follows. After centrifugation, the supernatant was removed, and only the cell pellet was recovered. The cell pellet was resuspended in 1.0×PBS (phosphate buffered saline) buffer solution, cell lysis was performed using a sonication equipment, and followed by centrifugation at 12,000 rpm for 15 minutes to separate only water-soluble proteins.

EXAMPLE 3

Method for Detecting Microorganisms with Probe

The double-stranded probe prepared in Example 1 was reacted with 100 µl of the crude extract extracted from the bacterial culture, and then the emission wavelength spectrum shown by the fluorophore was measured.

In addition, the double-stranded probe prepared above was reacted at 37° C. with 100 µl of the crude extract extracted from the bacterial culture while measuring the fluorescence intensity at an emission wavelength of 520 nm at a predetermined time interval (30 sec.), thereby measuring changes in fluorescence values during the reaction.

EXAMPLE 4

Identification on Detection of Microorganisms

Figure 2:
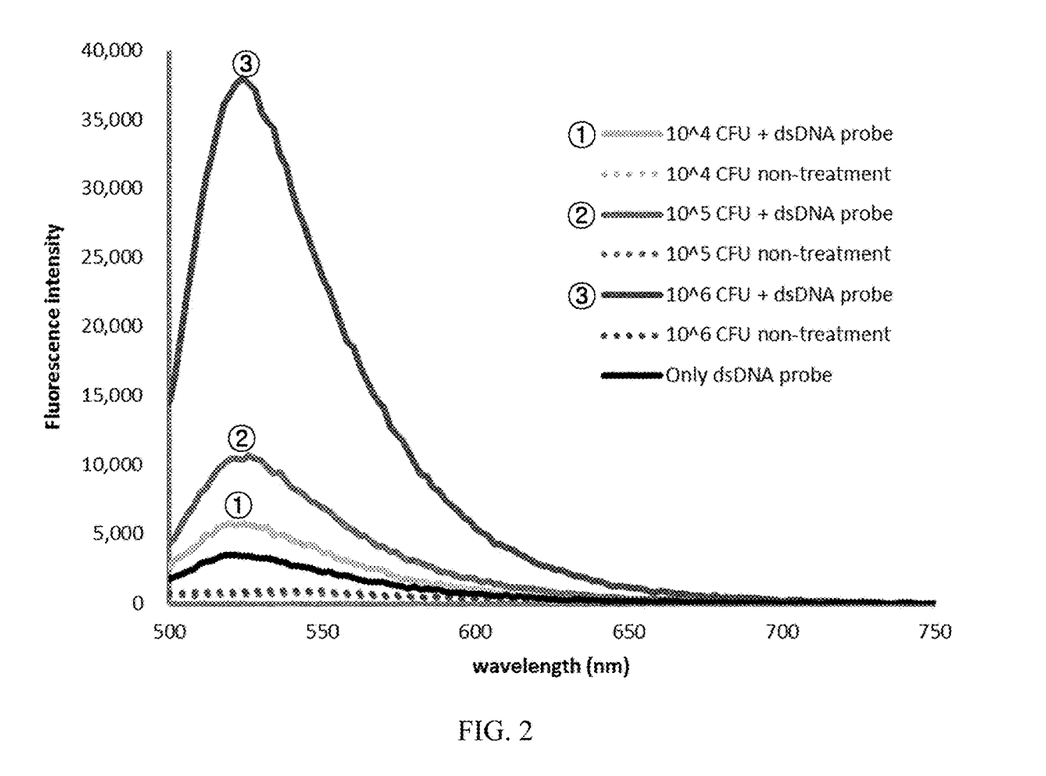
FIG. 2 illustrates results obtained by measuring the fluorescence development reactions of double-stranded probes by nucleases present in crude extracts.

Each of crude bacterial extracts at concentrations of $10^4$ CFU/100 µl, $10^5$ CFU/100 µl and $10^6$ CFU/100 µl was treated with the double-stranded probe (20 pmoles) for 30 minutes. The results are illustrated in FIG. 2. As illustrated in FIG. 2, it has been found that the higher the concentration of the crude extract extracted from the bacterial culture the higher the fluorescence intensity in the emission wavelength region of the fluorophore. Repeated experiments also showed that the fluorescence intensity was increased depending on the concentration of the crude extract.

The added double-stranded probe has an advantage that since the measurement equipment energizes the fluorophore separated from the quencher due to the nucleic acid degradation, the optical signal is consistently measurable without adding any additives, unlike the ATP-based measurement method. To demonstrate this, the crude extract and the double-stranded probe were mixed and then changes in fluorescence intensity over time were measured. The results are illustrated in FIG. 3.

Figure 3:
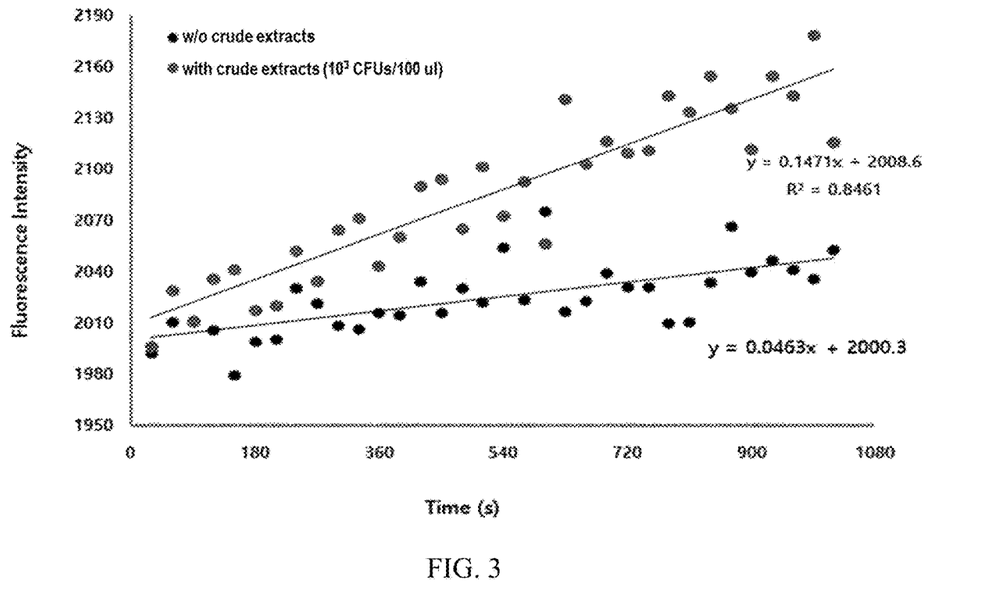
FIG. 3 illustrates results obtained by measuring changes in fluorescence intensity of double-stranded probes over time.

As illustrated in FIG. 3, it was observed that the fluorescence intensity values were not decreased even with the sample at a concentration of $10^3$ CFU/100 µl, and the fluorescence intensity was rather consistently increased due to the separation of the fluorophore from the quencher in the probe caused by the crude extract remaining in the sample. The increase rate of the fluorescence intensity was consistently maintained even after the lapse of time. Repeated experiments showed that the increasing slope value was constantly maintained depending on the concentration of the crude extract ($R^2$ value≈0.85).

On the contrary, it has been found that the slope value was maintained at 0.1 or less in the sample containing only the double-stranded probe as a control group, and thus, the fluorescence intensity was not increased even after the lapse of time, compared to the case where cells are present.

In order to identify the reaction in each of living cells and the dead cells, *E. coli* was cultured in LB medium, and then a part of the culture was heat-treated at 95° C. for 5 minutes. A crude extract corresponding to $10^6$ CFU/100 µl was recovered from each of the heat-treated culture and the untreated culture, and the amount of microorganisms was measured using treatment with a double-stranded probe, and luciferase and ATP. The results are illustrated in FIGS. 4 and 5.

Figure 4:
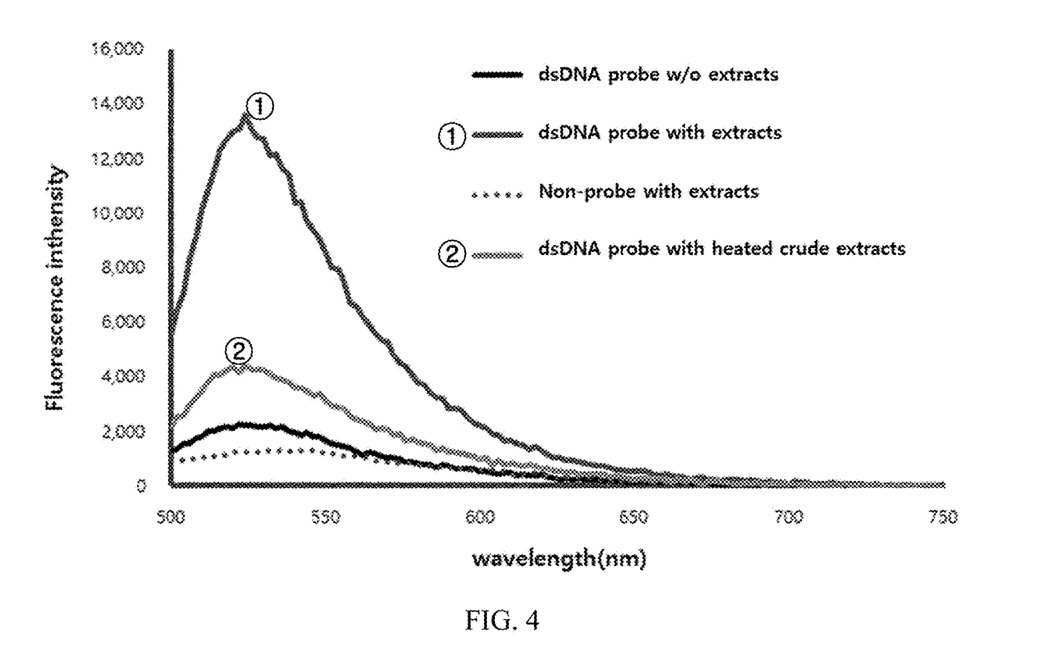
FIG. 4 illustrates results representing the reactions of double-stranded probes on each of the crude extracts of living *E. coli* and *E. coli* treated to death.
Figure 5:
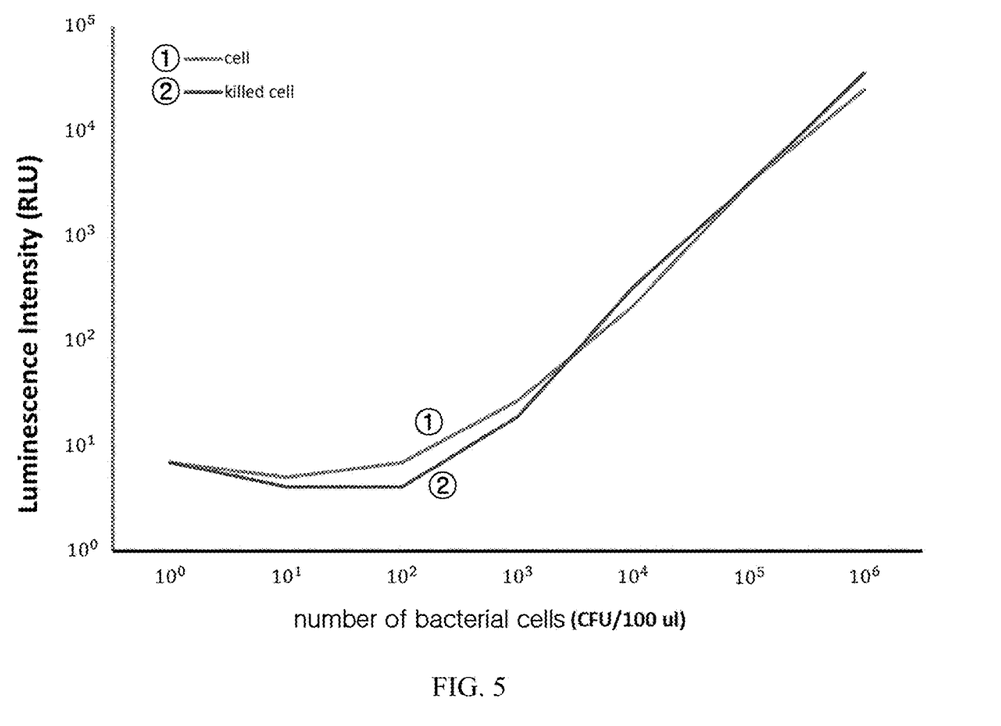
FIG. 5 illustrates results obtained by measuring and comparing the luciferase-based luminescence of each of living *E. coli* and *E. coli* treated to death.

As illustrated in FIG. 4, it has been found that in the case of the treatment with the double-stranded probe, the fluorescence value was noticeably decreased in the crude extract sample of heat-treated cells. On the contrary, as illustrated in FIG. 5, it has been found that in the case of the ATP-based measurement, the luminescence intensity value was not decreased in the dead microbial strain.

EXAMPLE 5

Identification of Constitutive Characteristics of the Present Probe

In order to identify the constitutional superiority of the double-stranded probes of the present invention, the present inventors additionally constructed single-stranded probes and probes with varying the number of mismatched nucleotides, and compared the respective degrees of detection for microorganisms.

The sequences of the probes constructed in this example are as follows:

Sequence of the single-stranded probe having a length of 18-mer (SEQ ID NO: 3) 5'-CCA CAG TCA CAT ACT CCA -3';

Sequence of the single-stranded probe having a length of 30-mer (SEQ ID NO: 4) 5'-AGT GTA CCA GCT GCA TGA CCT CTA AGT AGT -3';

Sequence of the double-stranded probe having a length of 36-mer (SEQ ID NOs: 1 and 2 as described above);

Sense sequence of the double-stranded probe having a length of 44-mer (SEQ ID NO: 5) 5'-ATC ATC TTC CCT CCC CGC ACC TAA AGG GTG CGG GGA GGG AAG AT -3'; and Antisense sequence of the double-stranded probe having a length of 44-mer (SEQ ID NO: 6) 5'- ATC TTC CCT CCC CGC ACC CTATTG GTG CGG GGA GGG AAG A -3'.

(The underlined indicates mismatched nucleotides.)

In the 36-mer and 44-mer double-stranded probes, the antisenses were designed to be shorter than their corresponding senses having a length of 36-mer and 44-mer in order to form sticky ends, and thus actually do not have the length of the indicated number. However, since such antisenses are antisenses to make double-stranded probes, they are named the same to avoid any confusion in designating names.

5-1. Identification on Comparison of Detection Depending on Types of Probes in *E. coli*

5-1-1. Measurement of Fluorescence Intensity Depending on Structures of Probes

In order to identify the superiority of the double-structure of the present double-stranded probes, single-stranded probes were constructed and measurements were performed for detection of *E. coli* as follows.

*E. coli* ($10^5$ CFU) lysed in a lysis buffer was treated with 18-mer and 30-mer single-stranded probes and 36-mer and 44-mer double-stranded probes, respectively, then, reacted at 37° C. for 30 minutes, and then the fluorescence intensity was measured.

Figure 6:
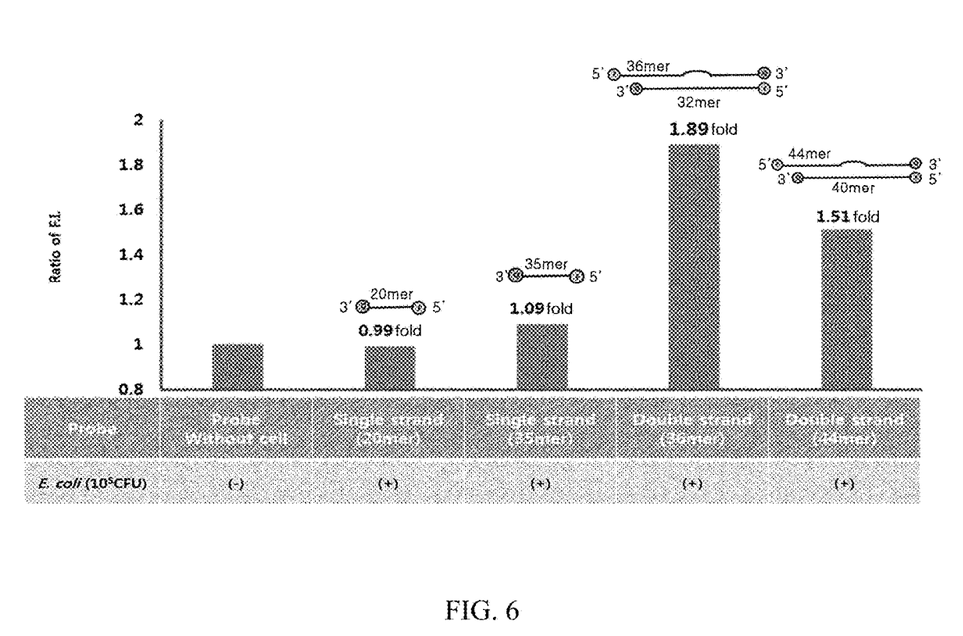
FIG. 6 illustrates results obtained by measuring fluorescence intensities of the present probes in *E. coli* depending on their structures.

As a result, as illustrated in FIG. 6, it has been found that the fluorescence intensity was increased greatest in the 36-mer double-stranded probe while the fluorescence intensity was hardly increased in the single-stranded probes.

5-1-2. Measurement of Fluorescence Intensity Depending on the Number of Mismatched Nucleotides in Probe In order to identify the superiority of the present double-stranded probes over the number of mismatches, probes with varying the number of mismatched nucleotides were constructed and measurements were performed for detection of *E. coli* as follows.

A probe was designed to have mismatched sequences inserted in the middle of the double-stranded probe such that a single-stranded endonuclease acts thereon. In this case, in order to identify the effect with the amount of mismatched sequences, *E. coli* ($10^5$ CFU) lysed in a lysis buffer was treated with each probe, reacted at 37° C. for 30 minutes, and then the fluorescence intensity was measured.

Figure 7:
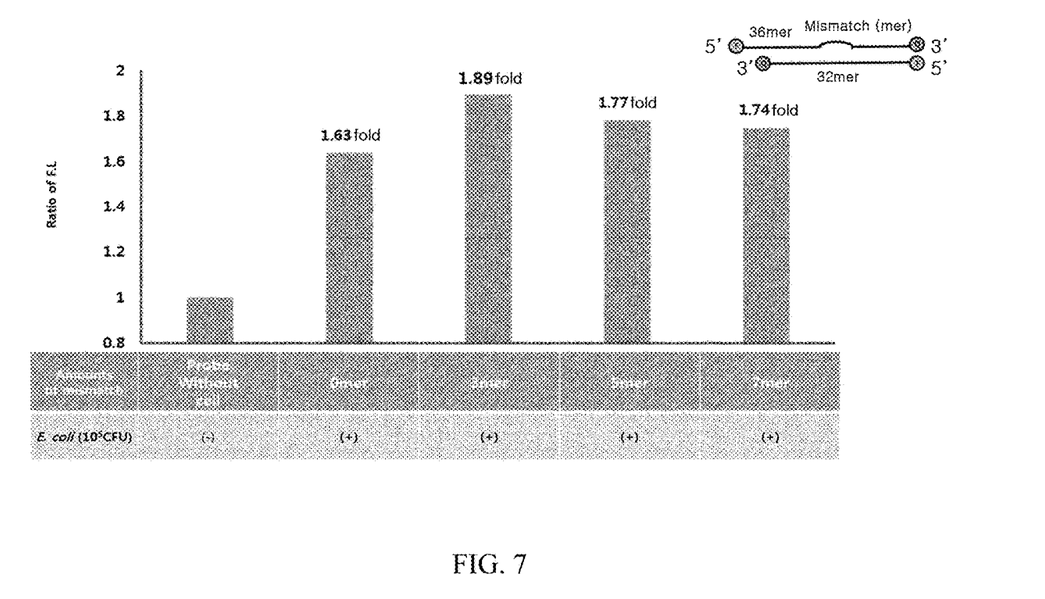
FIG. 7 illustrates results obtained by measuring fluorescence intensities of the present probes in *E. coli* depending on their number of mismatches.

As a result, as illustrated in FIG. 7, the fluorescence intensity was greatly increased in the probe having mismatches compared with the probe having no mismatch (0-mer) in which, among others, the fluorescence intensity was increased greatest in the probe having 3-mer of mismatches.

5-1-3. Fluorescence Signal Measurement in Living and Dead Bacteria

In order to identify the superiority of the present double-stranded probes with respect to false positive, measurements were performed for detection of living and dead *E. coli* bacteria under the following conditions.

*E. coli* ($10^5$ CFU) was either heated at 100° C. for 30 minutes or sterilized by treatment with 70% EtOH and clorox overnight. Each of the sterilized and living bacteria samples was treated with the probe to measure the increased fluorescence intensity.

Figure 8:
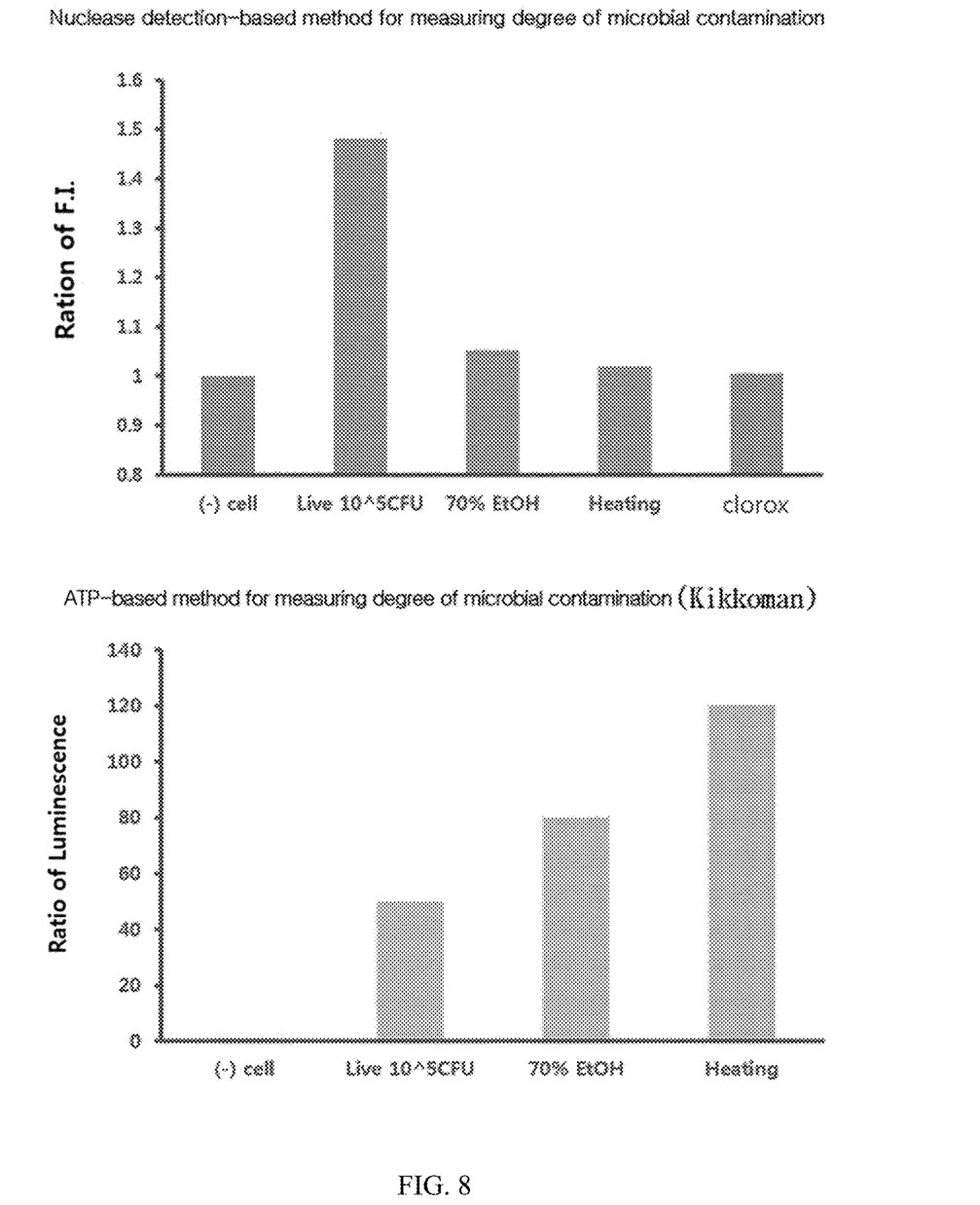
FIG. 8 illustrates results obtained by measuring fluorescence signals of the present probes in living and dead *E. coli* bacteria.

As a result, as illustrated in FIG. 8, in the case of the probes of the present invention, the fluorescence signal was greatly increased only in living cells, and the signal was greatly decreased in the sterilized samples.

On the other hand, when measured with the Kikkoman instrument, a representative conventional ATP-based measurement device for microbial contamination, sterilized samples exhibited similar to or even higher signals than those of living cells.

Therefore, it has been found that only living microorganisms can be selectively detected by the detection technique for degree of microbial contamination using the probes of the present invention.

5-1-4. Measurement Results for Fluorescence Intensity Depending on the Number of Cells In order to identify the superiority of the present double-stranded probes with respect to sensitivity, measurements were performed for detection of *E. coli* under the following conditions.

Living *E. coli* cells at the respective concentrations were treated with probes, reacted at 37° C. for 30 minutes, and then the fluorescence intensity was measured.

Figure 9:
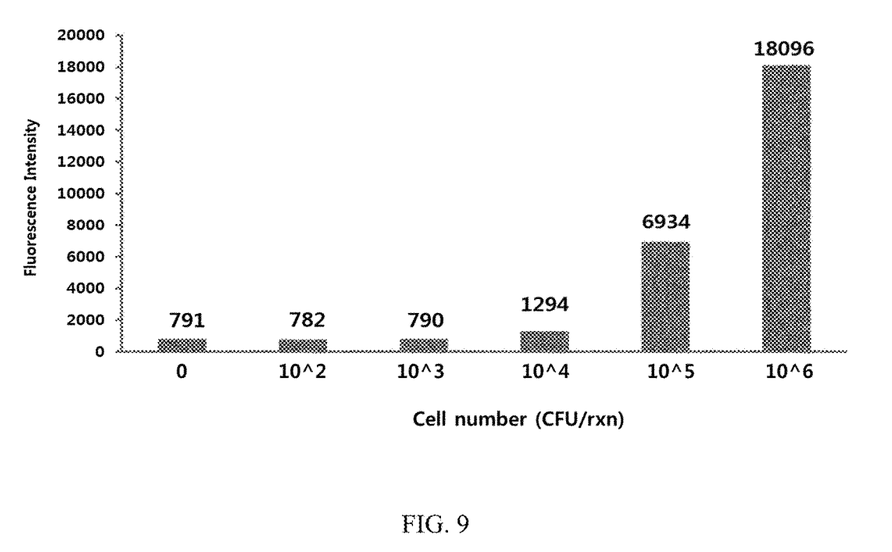
FIG. 9 illustrates results obtained by measuring fluorescence intensities of the present probes depending on the number of *E. coli* cells.

As a result, as illustrated in FIG. 9, it has been found that it is possible to detect the degree of contamination beginning from about $10^4$ CFU, through the detection technique for degree of microbial contamination using the probes of the present invention.

According to the common contamination standard for microorganisms, when $10^5$ CFU or more of microorganisms are detected, it is determined as contaminated. Although Kikkoman, which is usually used as a conventional detection device, can perform analysis beginning from $10^3$ CFU, significant measurement values appear starting from $10^4$ CFU in actual measurements. In consideration of the above, the detection technique for degree of microbial contamination using the probes of the present invention means that it is capable of detecting microorganisms, in a quick and easy way, at a sensitivity level similar to that of the conventional detection methods.

5-2. Measurement Results for Fluorescence Intensity Depending on the Number of Cells in *S. aureus*

In order to confirm the superiority of the present double-stranded probes with respect to sensitivity, measurements were performed for detection of *S. aureus* under the same conditions as in *E. coli*.

As in section 5-1-4, living *S. aureus* cells at the respective concentrations were treated with probes, reacted at 37° C. for 30 minutes, and then the fluorescence intensity was measured.

Figure 10:
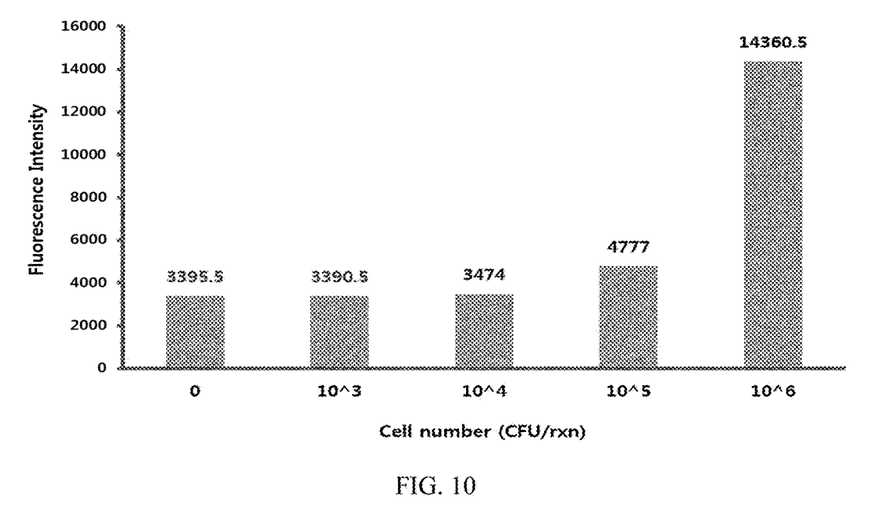
FIG. 10 illustrates results obtained by measuring fluorescence intensities of the present probes depending on the number of *S. aureus* cells.

As a result, as illustrated in FIG. 10, it has been found that it is possible to detect the degree of contamination beginning from about $10^4$ CFU also in *S. aureus*, through the detection technique for degree of microbial contamination using the probes of the present invention.

Accordingly, use of the detection technique for degree of microbial contamination using the probes of the present invention allows both Gram-negative bacteria and Gram-positive bacteria to be detected without false positive signals in a quick and easy way.

What is claimed is:

1. A composition for detecting microbial contamination, comprising:
 an agent for detecting nuclease in microorganism,
  wherein the agent is a double-stranded oligonucleotide;
  wherein the double-stranded oligonucleotide is a double-stranded oligonucleotide consisting of SEQ ID NO: 1 and SEQ ID NO: 2 or a double-stranded oligonucleotide consisting of SEQ ID NO: 5 or SEQ ID NO: 6;
  wherein one strand of the double-stranded oligonucleotide comprises a blunt end at the 5'-end or 3'-end; and the other strand of the double-stranded oligonucleotide comprises a sticky end on the opposite end of the blunt end;
  wherein the double-stranded oligonucleotide has 1 to 10 nucleic acid mismatches between both ends; and
  wherein the oligonucleotide comprises a fluorescent material and a quencher, attached to 3'-end, 5'-end, both ends, or anywhere between both ends.

2. The composition according to claim 1, wherein the sticky end comprises at least one mismatched base pair.

3. The composition according to claim 2, wherein the nucleic acid mismatches in the sticky end are present at the 3'-end.

4. The composition according to claim 1, wherein the fluorescent material is a luminous molecule, a metal ion, a complex compound, an organic dye, a conductor, a semiconductor, an insulator, a quantum dot, or a quantum wire.

5. A kit for detecting microbial contamination comprising the composition of claim 1.

6. A method for detecting microbial contamination, comprising:
 contacting a sample thought to be contaminated with microorganisms with a composition comprising an agent for detecting nuclease in microorganism, wherein the agent is a double-stranded oligonucleotide; wherein the double-stranded oligonucleotide is a double-stranded oligonucleotide consisting of SEQ ID NO: 1 and SEQ ID NO: 2 or a double-stranded oligonucleotide consisting of SEQ ID NO: 5 or SEQ ID NO: 6; wherein one strand of the double-stranded oligonucleotide comprises a blunt end at the 5'-end or 3'-end; and the other strand of the double-stranded oligonucleotide comprises a sticky end on the opposite end of the blunt end; wherein the double-stranded oligonucleotide has 1 to 10 nucleic acid mismatches between both ends; and wherein the oligonucleotide comprises a fluorescent material and a quencher, attached to 3'-end, 5'-end, both ends, or anywhere between both ends; and
 identifying fluorescence development in the sample, the presence of fluorescence is indicative of microbial contamination in the sample.

7. The method according to claim 6, wherein the method detects the presence of both Gram-negative and Gram-positive bacteria.

8. The method according to claim 6, wherein the microbial contamination is quantified by determining the intensity of the fluorescence.

9. An oligonucleotide for measuring nuclease activity:
 wherein the oligonucleotide is a double-stranded oligonucleotide consisting of SEQ ID NO: 1 and SEQ ID NO: 2 or a double-stranded oligonucleotide consisting of SEQ ID NO: 5 or SEQ ID NO: 6;
 wherein one strand of the double-stranded oligonucleotide comprises a blunt end at the 5'-end or 3'-end; and the other strand of the double-stranded oligonucleotide comprises a sticky end on the opposite end of the blunt end;
 wherein the double-stranded oligonucleotide comprises 1 to 10 mismatched base pairs between the blunt end and the sticky end; and wherein the oligonucleotide comprises a fluorescent material and a quencher, attached to 3'-end, 5'-end, both ends, or anywhere between both ends.

* * * * *

SEQUENCE LISTING

```
<160> NUMBER OF SEQ ID NOS: 6

<210> SEQ ID NO 1
<211> LENGTH: 36
<212> TYPE: DNA
<213> ORGANISM: Artificial Sequence
<220> FEATURE:
<223> OTHER INFORMATION: Double nucleic acid probe sense

<400> SEQUENCE: 1
acattaagtg taccagctgc atgaaagtac ttaata                      36

<210> SEQ ID NO 2
<211> LENGTH: 35
<212> TYPE: DNA
<213> ORGANISM: Artificial Sequence
<220> FEATURE:
<223> OTHER INFORMATION: Double nucleic acid probe antisense

<400> SEQUENCE: 2
tattaagtac tttcatgcaa acggtacact taata                       35

<210> SEQ ID NO 3
<211> LENGTH: 18
<212> TYPE: DNA
<213> ORGANISM: Artificial Sequence
<220> FEATURE:
<223> OTHER INFORMATION: Single nucleic acid probe

<400> SEQUENCE: 3
ccacagtcac atactcca                                          18

<210> SEQ ID NO 4
<211> LENGTH: 30
<212> TYPE: DNA
<213> ORGANISM: Artificial Sequence
<220> FEATURE:
<223> OTHER INFORMATION: Single nucleic acid probe

<400> SEQUENCE: 4
agtgtaccag ctgcatgacc tctaagtagt                             30

<210> SEQ ID NO 5
<211> LENGTH: 44
<212> TYPE: DNA
<213> ORGANISM: Artificial Sequence
<220> FEATURE:
<223> OTHER INFORMATION: Double nucleic acid probe sense

<400> SEQUENCE: 5
atcatcttcc ctccccgcac ctaaagggtg cggggaggga agat             44

<210> SEQ ID NO 6
<211> LENGTH: 40
<212> TYPE: DNA
<213> ORGANISM: Artificial Sequence
<220> FEATURE:
<223> OTHER INFORMATION: Double nucleic acid probe antisense
```

```
<400> SEQUENCE: 6
atcttccctc cccgcaccct attggtgcgg ggagggaaga                40
```